United States Patent [19]

Waldorf

[11] Patent Number: 4,815,839

[45] Date of Patent: Mar. 28, 1989

[54] INFRARED/VIDEO ELECTRONYSTAGMOGRAPHIC APPARATUS

[76] Inventor: Ronald A. Waldorf, 1206 South Bedford St., #1, Los Angeles, Calif. 90035

[21] Appl. No.: 81,013

[22] Filed: Aug. 3, 1987

[51] Int. Cl.⁴ .............................................. A61B 3/14
[52] U.S. Cl. .................................................. 351/210
[58] Field of Search ......................... 351/209, 210, 158

[56] References Cited

U.S. PATENT DOCUMENTS 3,542,457 11/1970 Balding et al. ...................... 351/209
3,609,016 9/1971 Jampolsky ............................ 351/209
4,145,122 3/1979 Rinard et al. ........................ 351/158

FOREIGN PATENT DOCUMENTS 3226096 2/1983 Fed. Rep. of Germany ...... 351/210

Primary Examiner—Rodney B. Bovernick
Assistant Examiner—P. M. Dzierzynski
Attorney, Agent, or Firm—Michael A. Painter

[57] ABSTRACT

A system for viewing and recording eye movement. Enclosed spherical eye pieces form goggles which are adapted to cover each of the eyes of the user to preclude the admission of ambient light. An infrared radiation source impinges upon the user's eye, the radiating energy being in the non-visible portion of the energy spectrum. The interior surface of each eye piece is coated with a surface adapted to reflect and disperse the radiating infrared energy. An infrared sensitive video camera is directly coupled to the goggle eye pieces, the camera being sensitive to infrared radiation. The output of the video camera is connected to monitoring apparatus for monitoring and recording the real-time observation of the user's eye movements.

11 Claims, 1 Drawing Sheet

INFRARED/VIDEO ELECTRONYSTAGMOGRAPHIC APPARATUS

BACKGROUND OF THE INVENTION

1. Field of the Invention

The present invention generally relates to optical viewing apparatus and, more particularly, to those systems which permit the viewing and recording of vertical, horizontal and rotary eye movements.

2. The evaluation of eye movements in patients is an important diagnostic tool in the clinical investigation of certain organic disorders. The techniques which are disclosed by the prior art have been generally designated as electronystagmography (ENG), electro-oculograph (EOG), photoelectronostagmography (PENG) and Frenzel lenses.

The systems defined as ENG and EOG differ only in the time constant of the recording equipment. ENG uses a time constant (AC recording) while EOG does not (DC recording). ENG and EOG use the inherent potential difference between the cornea and the retina of the eye (the corneal-retinal potential) as a means for recording eye movements. This technique is based on the fact that the eye acts as a dipole with the cornea being positively charged relative to the retina. The dipole axis is said to correspond to the visual axis. By placing electrodes at the skin surface adjacent to the eye orbit, the potential changes resulting from eye movements are recorded on appropriate types of polygraph instruments. The AC recording system of ENG mainly records eye movements, whereas eye positions as well as eye movements are recorded using the DC mode of EOG. There are inherent problems in both of these systems. Skin potential responses are in the same general frequency band as the eye movements, and in some subjects are of greater amplitude than the corneal-retinal potential. A second problem arises since the polarization of the skin electrodes causes baseline shifts in the recorded corneal-retinal potential, which may prevent the recording of the resulting eye movements.

Some of the electronic problems associated with ENG and EOG recording methods are overcome with the system defined as PENG. This technique, using infrared sensitive photoelectric cells mounted on goggles is able to detect the difference in reflected light off the sclera relative to the iris. The difference in reflectivity during eye movement is translated into an electrical signal which can be recorded on a polygraph instrument similar to that used with ENG or EOG methods. With this technique, the problem of electropolarization or skin potential artifacts is eliminated as no connection is made to the skin. However, eyelid tremor and blinking still cause artifacts which complicate the analysis of the polygraph traces. The major disadvantage of PENG is that testing must be done with the eyes open and in some cases, the infrared light used was of a lower wave length and could be seen by the patient after a period of dark adaptation. Thus, optic fixation when present will reduce or inhibit the nystagmus. The problem of resolving eye position with PENG is the same as that encountered with electro-techniques.

Frenzel lenses are glasses which are plus 20 diopter lenses, having a built-in light source. They allow for direct observation of eye movements because the lenses act as magnifiers. The problems which are inherent in this system is that they do not provide total elimination of optic fixation, and they do not give a permanent record of eye movement responses. The major disadvantage of all the other techniques is it is impossible to record rotary eye movements, i.e., movement of the eye about the visual axis.

For electrode methods, it is because the dipole is in the plane of the visual axis and therefore there is no change in its recording at the electrode sites during a rotary eye movement. And for PENG, the reflectivity of the sclera (the white of the eye) and the iris (the colored center portion) does not change relative to the infrared sensors during rotary eye movement.

The present invention substantially resolves the problems which are inherent in systems disclosed by the prior art. The present invention employs an infrared radiation source which illuminates the patient's eyes with non-visible infrared radiation. The infrared radiation source is affixed directly to spherical eye pieces mounted over the patient's eyes or the emitted radiation can be transmitted through the use of a fiberoptic light bundle. The goggle eye pieces are fully enclosed to preclude the entry of any ambient light. The interior surface of the eye pieces are coated with a reflective surface which will substantially reflect and disperse the emitted infrared energy. The infrared radiation reflected from the eye of the subject is monitored by a coupled video sensor. The reflected radiation is monitored directly or can be transmitted through a fiberoptic light bundle to a relay lens of a video camera which is adapted for infrared viewing. The output of the video camera is coupled to a monitor and recorder to provide for subsequent analysis. Since the present invention is fully operational even when the patient moves his head, eye movements following head movements can be properly recorded. In addition, since ambient light is precluded and the impinging radiation is outside of the band width of visible light, the problem of optic fixation is fully resolved.

SUMMARY OF THE INVENTION

The present invention provides for the sensing, monitoring and recording of eye movements by detecting reflected infrared radiation which impinges upon the eye of the subject. Enclosed goggles comprising a pair of spherical eye pieces cover the eyes of the subject to prevent any ambient light from impinging upon the subject's eyes. The interior surface of each of the spherical eye pieces is sufficient to reflect and fully disperse radiated energy in the infrared portions of the energy spectrum. An infrared light emitting source transmits infrared radiation directly into the sphere, which integrates and dispenses the radiation to the eye. Detection of the reflected infrared radiation is through a directly coupled video camera sensitized to radiation in the infrared range. The output of the video camera is coupled to recording equipment for real time observation or off-line analysis of the observed eye movements.

Continuous sensing and monitoring occurs independent of any optic fixation since the infrared radiation impinging upon the subject's eye is outside of the visible light range.

It is therefore an object of the present invention to provide an improved apparatus for observing and recording the subject's eye movement.

It is another object of the present invention to provide an apparatus for observing the recording eye movement which is impervious to the subject's head movement.

It is still another object of the present invention to provide apparatus for observing and recording a subject's eye movement which includes rotary eye movement.

It is still yet another object of the present invention to provide an apparatus for observing and recording eye movement which is simple and inexpensive to fabricate.

The novel features which are believed to be characteristic of the invention, both as to its organization and method of operation, together with further objectives and advantages thereof, will be better understood from the following description considered in connection with the accompanying drawing in which a presently preferred embodiment of the invention is illustrated by way of example. It is to be expressly understood, however, that the drawing is for the purpose of illustration and description only and is not intended as a definition of the limits of the invention.

DESCRIPTION OF THE PRESENTLY PREFERRED EMBODIMENT

Figure 1:
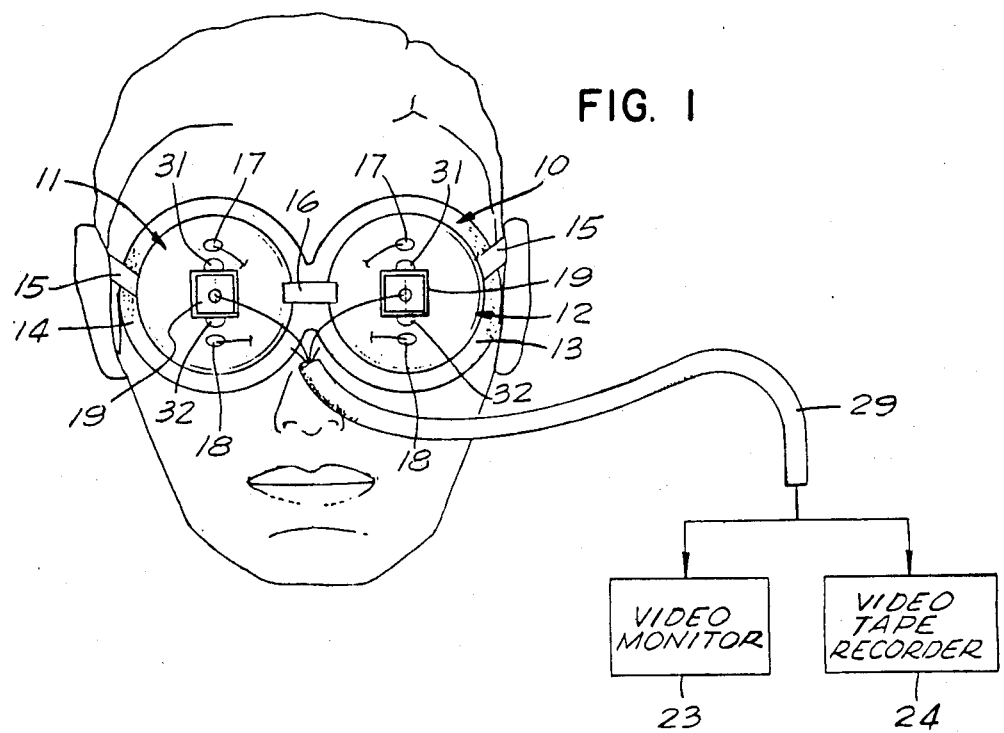
FIG. 1 illustrates the preferred embodiment of the present invention utilizing a directly coupled infrared/video sensing apparatus.
Figure 2:
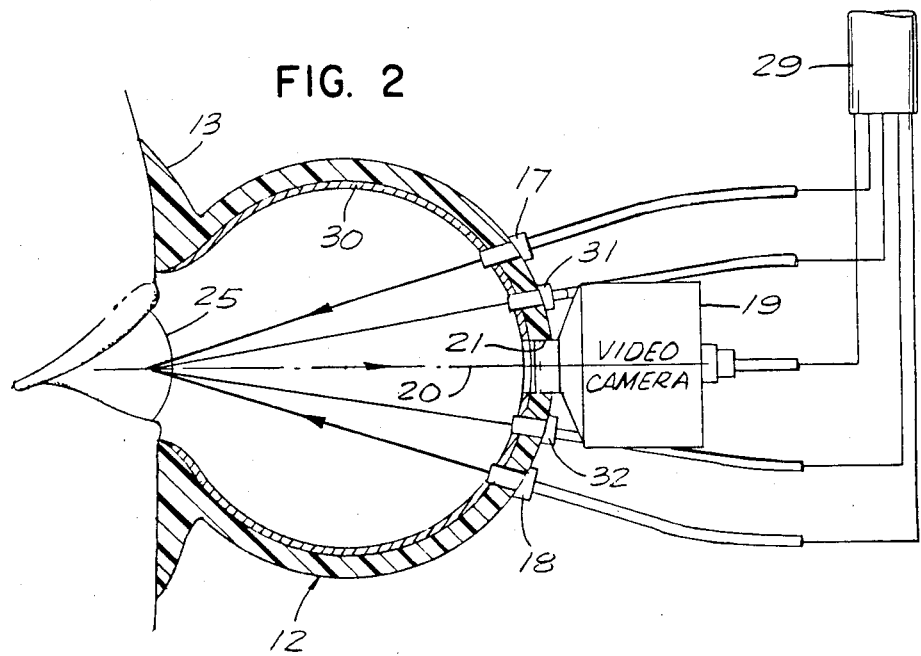
FIG. 2 is a partial cross-sectional view of the relationship between a user's eye and the spherical goggle eye piece of the preferred form of the present invention infrared/video sensing and monitoring apparatus.

An understanding of the present invention can be best gained by reference to FIGS. 1 and 2 wherein the preferred form of the present invention apparatus is shown. As discussed, one of the basic needs inherent in any clinical device is the ability to record eye movement which occur as a result of the movement of the user's head.

Referring now to FIG. 1, goggle assembly 10 is mounted across the subject's eye to preclude any ambient light from impinging upon the eyes of the subject. By excluding ambient light from the testing area, optic fixation is eliminated and thereby permits a permanent record of true eye movement responses. Goggle assembly 10 (FIG. 1) comprises a pair of spherical eye pieces 11 and 12 which are intended to totally enclose the eye sockets of the user and totally exclude any ambient light from impinging upon the subject's eye. As can be seen in FIG. 2, eye piece 12 has an integral shield member 13 which lies along the side of the face of the user blocking out ambient light. Eye piece 11 employs a shield 14 in precisely the same manner as used with respect to eye piece 12 and shield 13. The interior of eye pieces 11 and 12 are spherical in shape. Shields 13 and 14 are typically fabricated of a flexible material which will conform to the undulations of the subject's face. An elastic band 15 is coupled to the respective eye pieces 11 and 12 to secure goggle assembly 10 in position. Since the present invention is to be usable irrespective of the user, eye pieces 11 and 12 are joined by hinged coupling 16 which is affixed intermediate eye pieces 11 and 12, respectively.

Since an object of the present invention is to permit monitoring of eye movement without the problem of optic fixation, energy in the infrared range is used to impinge upon the subject's eye and to provide images. The emission of energy in the infrared range occurs at wave lengths in the range invisible to humans, i.e., beyond the red end of the spectrum of visible light. The preferred form of the present invention employs a pair of infrared radiating members 17 and 18, these members typically being infrared light emitting diodes (IR-LED). As shown in FIGS. 1 and 2, IR-LEDs 17 and 18 are mounted through the walls of eye pieces 11 and 12 in respective positions above and below optic axis 20. Optic axis 20 is defined as a line bisecting the subject's pupil and the directly coupled video camera 19. Although it is understood the preferred embodiment employs infrared radiation sources 17 and 18, these could be replaced with an assembly which employs an incandescent light source which emits visible and non-visible, i.e., infrared, light. In the alternative embodiment, the visible light source is coupled to an infrared filter which filters out all light in the visible and ultraviolet frequency band and permits only a narrow bandwidth in the infrared, non-visible range, i.e., approximately 0.85–1.00 microns.

Video camera 19 is a commercially available, low-light level video camera which is receptive to the non-visible, infrared image of the eye. As an example, a Pulnix Model TM540CCD can be used to implement video camera 19. The reduced size of video camera 19 permits it to be directly affixed to spherical eye pieces 11 and 12 through an aperture 21 which lies on optic axis 20. After passing through a lens, the video camera 19 processes the video signal in a conventional manner. The output signal of video camera 19 is transmitted by an electronic cable 29 to a standard video monitor 23 which can be used for real-time monitoring operations and to a video tape recorder 24 which will record all output signals and provide the ability to perform off-line analysis of the eye movement responses, or a computer for real-time analysis.

The embodiment of the spherical eye pieces 11 and 12, coupled with the relative positioning of IR-LEDs 17 and 18 and video camera 19 as shown in FIG. 2 permit complete sensing and monitoring of the horizontal, vertical, oblique and rotational movement of the user's eye. To achieve complete and detailed sensing and monitoring of the above-identified eye movement in the absence of a source of optic fixation, i.e., light in visible range of the spectrum, the interior surface of each spherical eye piece 11 and 12 is coated with a layer 30 of reflective material which will substantially reflect and thoroughly disperse the energy emitted from IR-LEDs 17 and 18. Since one of the objectives of the present invention is to permit accurate monitoring of rotary eye movement, i.e., rotation of the eye about its visual axis, the structure shown in FIG. 2 provides substantially improved capabilities.

To monitor the rotary component of eye movement, it is necessary to pick up some landmark on the iris 25. As stated, the embodiment of the present invention shown in FIGS. 1 and 2 provides for placement of imaging video camera 19 along optic axis 20. Since the iris 25 has a substantial number of radially directed striations, the infrared radiation which is reflected and sensed by video camera 19 will highlight the striations thereby permitting the systems to monitor the rotary component of the subject's eye movement. Although it is understood that the preferred embodiment of the present invention employs a spherical profile for eye pieces 11 and 12, it is understood alternative geometric shapes can be employed so long as there is substantially uniform reflection and dispersion of the emitted infrared energy within the volume enclosed by eye pieces 11 and 12.

It can therefore be seen that the present invention provides a device which substantially resolves difficulties inherent in those devices disclosed by the prior art. The present invention provides for continuous sensing, monitoring and recording of eye movements irrespective of any position of the subject's head. Since the eye being monitored is being fully "illuminated" by radiation in the infrared range, the light is invisible to the subject thereby eliminating optic fixation. In addition, since eye movement can be monitored irrespective of any head movement, the physiological responses of the eye which will occur as a result of head movement can be monitored thus providing for the collection of data which has heretofore been difficult or impossible to obtain.

During some procedures, it is desirable to provide sources of optic fixation with eye pieces 11 and 12. The present invention provides the ability to monitor the eye during impingement of a fixed source or sources visible light for the purpose of establishing optic fixation. As can be seen in FIG. 2, light sources 31 and 32 provide sources of light energy in the visible range and can be implemented by conventional light emitting diodes for the application of a point source for visual fixation. All controls of IR-LEDs 17 and 18, LEDs 31 and 32, and the transmission of video signals to video monitor 23 and video tape recorder 24 are routed through cable 29 which is conventionally coupled to goggle assembly 10.

I claim:

1. An infrared/video electronystagmographic apparatus for monitoring the eye movement of a subject comprising:
   (a) first and second hollow eye pieces, each having an interior surface and first and second apertures therethrough, the first aperture being adapted to be fitted about an eye orbit of a subject;
   (b) sealing means for excluding substantially all visible light from impinging upon the eyes of the subject, precluding the subject from viewing anything within or external to said eye pieces, said sealing means being coupled to said first and second eye pieces about the first apertures therein;
   (c) reflecting means for reflecting and dispersing energy in the infrared range of the spectrum disposed upon the interior surface of the eye pieces;
   (d) infrared source means for radiating a source of infrared radiation in the invisible portion of the energy spectrum at the eye of the subject, infrared source means being coupled to each of said first and second eye pieces, each being in communication with the interior surface of said eye pieces; and
   (e) video sensing means for sensing reflected infrared images of horizontal, vertical, oblique and rotary eye movement, said video sensing means being coupled to said first and second eye pieces through a second aperture disposed therein diametrically opposed to said first aperture.

2. An infrared/video electronystagmographic apparatus as defined in claim 1 wherein said hollow eye pieces are spherical.

3. An infrared/video electronystagmographic apparatus as defined in claim 2 wherein said video camera means lies along the optic axis of said eye piece and said infrared source means is mounted at an oblique angle to the optic axis.

4. An infrared/video electronystagmographic apparatus as defined in claim 3 wherein the oblique angle between the optic axis and the infrared source means is substantially 15° of arc.

5. An infrared/video electronystagmographic apparatus as defined in claim 1 wherein said infrared source means comprise infrared, light emitting diodes.

6. An infrared/video electronystagmographic apparatus as defined in claim 1 wherein said infrared source means comprises a source of visible light and an infrared filter coupled thereto, said infrared filter outputting radiation having wave lengths greater than that of visible light.

7. An infrared/video electronystagmographic apparatus as defined in claim 1 further including an illuminating source means for radiating a source of light in the visible portion of the spectrum at the eye of the subject, said illuminating source means coupled to said first and second eye pieces.

8. An infrared/video electronystagmographic apparatus as defined in claim 7 wherein said illuminating source means comprises a light emitting diode radiating energy in the visible spectrum.

9. An infrared/video electronystagmographic apparatus for monitoring the eye movement of a subject comprising:
   (a) a goggle assembly comprising first and second hollow spherical eye pieces each having an interior surface and first and second apertures therethrough, the first aperture being adapted to be fitted about the eye orbit and optic axis of the subject, each of said eye pieces being extended about the eye orbit of the subject to exclude all visible, ambient light from impinging upon the eyes of the subject whereby the subject is precluded from viewing anything within or external to said goggle assembly;
   (b) a reflective coating disposed upon the interior surface of said first and second eye pieces, said reflective surface adapted to reflect and disperse energy in the infrared range of the spectrum;
   (c) video sensing means for sensing reflected infrared images of horizontal, vertical, oblique and rotary eye movements, said video sensing means being coupled to said eye piece through a second aperture therein, said second aperture being disposed through said eye piece diametrically opposed to said first aperture and in alignment with the optic axis; and
   (d) at least one infrared emission source emitting radiation having wave lengths in the infrared range, said infrared emission source coupled to said eye pieces at an oblique angle with respect to said optic axis and the video sensing means whereby infrared radiation reflected from the eye of the subject is reflected toward the video sensing means.

10. An infrared/video electronystagmographic apparatus as defined in claim 9 wherein two infrared emission sources are coupled to each of said eye pieces.

11. An infrared/video electronystagmographic apparatus as defined in claim 9 further including an illuminating emission source of radiation having wave lengths in the visible range coupled to said of said eye pieces whereby visible light is radiated upon the eye of the subject.

* * * * *